US006235498B1

(12) United States Patent
Mather et al.

(10) Patent No.: US 6,235,498 B1
(45) Date of Patent: *May 22, 2001

(54) METHOD FOR CULTURING RECOMBINANT CELLS

(75) Inventors: Jennie P. Mather, Millbrae; Axel Ullrich, Portola Valley, both of CA (US)

(73) Assignee: Genentech, Inc., So. San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/845,698

(22) Filed: Apr. 25, 1997

Related U.S. Application Data

(63) Continuation of application No. 08/633,638, filed on Apr. 17, 1996, which is a continuation of application No. 08/420,619, filed on Apr. 12, 1995, now abandoned, which is a continuation of application No. 08/222,498, filed on Apr. 4, 1994, now abandoned, which is a continuation of application No. 07/560,482, filed on Jul. 13, 1990, now abandoned, which is a continuation of application No. 07/097,472, filed on Sep. 11, 1987, now abandoned.

(51) Int. Cl.[7] .................................................. C12P 21/02
(52) U.S. Cl. ..................................... 435/69.1; 435/440
(58) Field of Search ................................ 435/69.1, 70.3, 435/91.1, 172.3, 320.1, 172.1, 23.51, 440; 536/23.51

(56) References Cited

U.S. PATENT DOCUMENTS

| | | | |
|---|---|---|---|
| 4,673,649 | 6/1987 | Boyce et al. | 435/240 |
| 4,740,461 | * 4/1988 | Kaufman | 435/68 |

FOREIGN PATENT DOCUMENTS

| | | | |
|---|---|---|---|
| 0163404 | 12/1985 | (EP) . | |
| 0171142 | 2/1986 | (EP) . | |
| 63-28386 | 2/1988 | (JP) | C12N/5/00 |
| 8600619 | 1/1986 | (WO) | C07H/15/12 |
| WO 8600619 | 1/1986 | (WO) | C07H/17/00 |

OTHER PUBLICATIONS

U.S. application No. 07/083,758, Capon et al., filed Aug. 7, 1987.

Aldred et al., "Synthesis of Rat Transferrin in *Escherichia coli* Containing a Recombinant Bacteriophage" *Biochem. & Biophys. Res. Comm.* 122(3):960–965 (1984).

Bottenstein et al., "The Growth of Cells in Serum–Free Medium" *Methods in Enzymology* 58:94–109 (1979).

Fry et al., "Transformation of Diploid Human Fibroblasts by DNA Transfection with v–Sis Oncogene" *J. of Cell Physio* 128:313–321 (1986).

Gruss et al., "Expression of Simian Virus 40–Rat Preproinsulin Recombinants in Monkey Kidney Cells: Use of Preproinsulin RNA Processing Signals" *Proc. Natl. Acad., Sci., USA* 78(1):133–137 (1981).

Lang et al., "Expression of a Hemopoietic Growth Factor cDNA in a Factor–Dependent Cell Line Results in Autonomous Growth and Tumorigenicity" *Cell* 43:531–542 (1985).

Lau et al., "Amplification and Expression of Human α–Globin Genes in Chinese Hamster Ovary Cells" *Molecular & Cellular Biology* 4(8):1469–1475 (1984).

Laub et al, "Expression of the Human Insulin Gene in an Alternate Mammalian Cell and in Cell Extracts" *Journal of Biological Chemistry* 258(10):6037–6042 (1983).

Laub et al., "Expression of the Human Insulin Gene and cDNA in a Heterologous Mammalian System" *Journal of Biological Chemistry* 369(10):6043–6050 (1983).

Lomedico, "Use of Recombinant DNA Technology to Program Eukaryotic Cells to Synthesize Rat Proinsulin: A Rapid Expression Assay for Cloned Genes" *Proc. Natl. Acad. Sci. USA* 79:5798–5802 (1982).

Mather et al., "The Growth of Mouse Melanoma Cells in Serum–Free Hormone Supplemented Medium" *Exptl. Cell Res.* 120:191–200 (1979).

Mather, J.P. *Mammalian Cell Culture–The Use of Serum–Free Hormone–Supplemented Media*, New York:Plenum Press (1984).

McKnight et al., "Expression of the Chicken Transferrin Gene in Transgenic Mice" *Cell* 34:335–341 (1983).

Mendiaz et al., "A Defined Medium for and the Effect of Insulin on the Growth, Amino Acid Transport, and Morphology of Chinese Hamster Ovary Cells, Cho–K1 (CCL 61) and the Isolation of Insulin Independent Mutants" *In Vitro Cell & Dev. Biol.* 22(2):66–74 (1986).

Moore et al., "Expressing a Human Proinsulin cDNA in a Mouse ACTH–Secreting Cell. Intracellular Storage, Proteolytic Processing, and Secretion on Stimulation" *Cell* 35:531–538 (1983).

Peavy et al., "In Vitro Activity of Biosynthetic Human Proinsulin: Receptor Binding and biologic Potency of Proinsulin and Insulin in Isolated Rat Adipocytes" *Diabetes* 33:1062–1067 (1984).

Perez–Infante et al., "Differential Regulation of Testicular Transferrin and Androgen–Binding Protein Secretion in Primary Cultures of Rat Sertoli Cells" *Endocrin.* 118(1):383–391 (1986).

Perez–Infante et al., "The Role of Transferrin in the Growth of Testicular Cell Lines in Serum–Free Medium" *Exp. Cell Res.* 142:325–332 (1982).

(List continued on next page.)

*Primary Examiner*—James Ketter
(74) *Attorney, Agent, or Firm*—Sean A. Johnston; Atulya R. Agarwal

(57) ABSTRACT

A method for culturing a recombinant host cell comprising: determining a polypeptide factor for a polypeptide factor-dependent host cell; transforming said host cell with nucleic acid encoding said polypeptide factor; transforming the host cell with nucleic acid encoding a desired protein; and, culturing the transformed host cells in a medium lacking the polypeptide factor.

7 Claims, 9 Drawing Sheets

OTHER PUBLICATIONS

Reitz et al., "Lowering Extracellular Na+ Concentration Releases Autocrine Growth Factors from Renal Epithelial Cells" *Proc. Natl. Acad. Sci. USA* 83:4764–4768 (1986).
Rosenthal et al., "Expression in Rat Fibroblasts of a Human Transforming Growth Factor–α cDNA Results in Transformation" *Cell* 46:301–309 (1986).
Fry, D.G., et al J. of Cell Physio 001 128 pp 313–321 (1986).*
Lau, Y–F. et al Mol Cell Biol. vol. 4 pp 1469–1475 (1984).*
Mather, J.P. Mammalian Cell Culture, Mather, Ed., (Plenum Pub. Corp. 1984) 167–193.
Mather et al. Exp. Cell Res. 120:191–200 (1979).
Bottenstein et al, Methods in Enzym. 58:94–109 (1979).
Rosenthal et al., Cell 46:301–309 (1986).
Lang et al., Cell 43:531–542 (1985).
Perez–Infante et al., Endocrin. 118(1):383–391 (1986).
Perez–Infante et al., Exp. Cell Res. 142:325–332 (1982).
Mendiaz et al., In Vitro Cell. & Dev. Biol. 22(2):66–74 (1986).
Walsh Reitz et al., P.N.A.S. 83:4764–4768 (1986).
Gross & Khoury, PNAS USA, 78(1):133–137 (1981).
Lomedico, PNAS USA, 79:5798–5802 (1982).
Laub & Rutter, J. Biol. Chem., 258(10):6043–6050 (1983).
Moore et al., Cell, 35:531–538 (1983).
Laub et al., J. Biol. Chem., 258(10):6037–6042 (1983).
Peavy et al., Diabetes, 33:1062–1067 (1984).
McKnight, et al., Cell 34:335–341 (1983).
Aldred, et al., Biochem. Biophys. Res. Commun. 122(3) : 960–965 (1984).

* cited by examiner

METHOD FOR CULTURING RECOMBINANT CELLS

CROSS-REFERENCE TO RELATED APPLICATIONS

This is a continuation of applications Ser. 08/633,638 filed Apr. 17, 1996, which is a continuation of Ser. No. 08/420,619 filed Apr. 12, 1995 (now abandoned), which is a continuation of application Ser. No. 08/222,498 filed Apr. 4, 1994 (now abandoned), which is a continuation of application Ser. No. 07/560,482 filed Jul. 13, 1990 (now abandoned), which is a continuation of application Ser. No. 07/097,472 filed Sep. 11, 1987 (now abandoned), and which applications are incorporated herein by reference and to which applications priority is claimed under 35 USC §120.

U.S. Ser. No. 07/097,246 filed of even date, relates to a method of preparing heterologous polypeptides in a recombinant host cell and enhancing the yields of said heterologous polypeptides by transfecting said host cell with a nucleic acid encoding an oncogene and culturing those transformed host cells.

FIELD OF THE INVENTION

This invention relates to methods for culturing vertebrate host cells transformed to produce a desired protein. In particular it relates to the use of recombinant technology to create host cells which will produce factors necessary for their survival and growth in culture.

BACKGROUND OF THE INVENTION

The last decade has seen an explosive growth in the knowledge of molecular biology and commercialization of that knowledge. Great success has been had in the cloning and expression of genes encoding proteins that were previously available in very small amounts, such as human growth hormone, tissue plasminogen activator and various lymphokines, to name just a few. Initially attempts were made to produce these proteins in bacterial or yeast expression systems. Many proteins may be preferably produced in cell culture. The reasons influencing one to use cell culture are: glycosylation of the desired protein, ease of purification of secreted products, and correct protein processing with correct folding and disulfide bond formation.

Once the gene encoding the desired protein is expressed in a mammalian cell line, its production must then be optimized. Optimization of protein yield in cell culture may be made by various means. Improvement may be obtained, for example by optimizing the physicochemical, nutritional, and hormonal environment of the cell.

Mammalian cells in vivo are in a carefully balanced homeostatic environment. The advantages of obtaining a completely defined medium for the growth of cells in vitro were recognized very early in the history of cell culture. (Lewis, M. R. and Lewis, W. H., Anat. Rec. 5:277 [1911]). Defined medium typically refers to the specific nutritional and hormonal chemicals comprising the medium required for survival or growth. Most cell types have stringent requirements as to the optimal range of physical parameters for growth and performance. Physicochemical parameters which may be controlled in different cell culture systems, for example, are: temperature, pH, $pO_2$, and osmolarity. The nutritional requirements of cells are usually provided in standard media formulations developed to provide an optimal environment. Nutrients can be divided into several categories: amino acids and their derivatives, fatty acids, complex lipids, carbohydrates, sugars, vitamins and nucleic acid derivatives. Not only the absolute requirements, but the relative concentrations of nutrients must be optimized for each individual cell type.

Most cell types will not grow and/or secrete proteins optimally in medium consisting only of nutrients, even when the nutritional components are optimized. It is for this reason that serum has remained an essential medium component for the growth of cells in culture. Various experiments led to the hypothesis that the role of serum in cell culture was to provide a complex of hormones that were growth-stimulatory for a given cell type. (Sato, G. H. et al., in *Biochemical Action of Hormones*, Vol.III [G. Litwak, ed.] Academic Press, N.Y., page 391). A pituitary cell line was grown in serum-free medium supplemented with hormones, growth factors, and transferrin. (Hayashi, I. and Sato, G., Nature [Lond] 159:132 [1976]). Subsequently, hormone-supplemented serum-free conditions were developed for the growth of several cell lines originating from different tissues (Mather, J. and Sato, G., Exp. Cell Res. 120:191 [1979]; Barnes, D. and Sato, G., Cell 22:69 [1981]). These studies led to several conclusions concerning the growth of cells in serum-free medium. Serum can be replaced by a mixture of hormones, growth factors, and transport proteins. The required supplements (containing the hormones, growth factors and transport proteins) to serum-free medium may differ for different cell types. The supplements, traditionally, have been provided as part of complex biological mixtures such as serum or organ extracts. The "hormonal" milieu may be optimized to reduce or eliminate the need for undefined growth factors, remove inhibitory factors, or provide critical hormones at desirable levels.

Cells frequently require one or more hormones from each of the following groups: steroids, prostaglandins, growth factors, pituitary hormones, and peptide hormones. Most cell types require insulin to survive in serum-free media. (Sato, G. H. et al. in *Growth of Cells in Hormonally Defined Media*, [Cold Spring Harbor Press, N.Y., 1982]). Certain mutant cell lines have been reported which are insulin-independent. (Mendiaz, E. et al., In Vitro Cell. & Dev. Biol. 22 [2]:66 [1986]; Serrero, G., In Vitro Cell. & Biol. 21[9]:537 [1985]). In addition to the hormones, cells may require transport proteins such as transferrin (plasma iron transport protein), ceruloplasmin (a copper transport protein), and high density lipoprotein (a lipid carrier) to be added to cell media. The set of optimal hormones or transport proteins will vary for each cell type. Most of these hormones or transport proteins have been added exogenously or, in a rare case, a mutant cell line has been found which does not require a particular factor.

Recently, cellular proliferation has been studied to elaborate the events necessary to lead from quiescent growth arrest to the cellular commitment to proliferate. Various factors have been found to be involved in that transformation. These transformed cells have been found to produce peptide growth factors in culture. (Kaplan, P. L. et al., PNAS 79:485–489 [1982]). The secretion from a cell of a factor to which that same cell can respond has been referred to as an "autocrine" system. Numerous factors have been described as autocrine: bombesin, interleukin-2 (Duprez, V. et al. PNAS 82:6932 [1985]); insulin, (Serrero, G. In Vitro Cellular & Dev. Biol. 21 [9]:537 [1985]); transforming growth factor alpha (TGF-α), platelet-derived growth factor (PDGF); transforming growth factor-beta (TGF-β), (Sporn, M. B. & Roberts, A. B., Nature 313:745 [1985]); sarcoma growth factor (SGF), (Anzano, M. A. et al., PNAS 80:6264 [1983]); and, hemopoietic growth factor, granulocyte-macrophage colony stimulating factor (GM-CSF), (Lang, R. A. et al., Cell 43:531 [1985]).

It is an object of the present invention to provide a defined medium for particular recombinant host cells. Another object of this invention is to eliminate problems associated with the supply of necessary polypeptide factors for the maintenance and growth of recombinant host cells. For example, certain polypeptide factors, such as insulin, are unstable in some culture conditions. It is an object of the invention to provide a local environment for the host cell that is optimal for growth or survival. More particularly, it is an object of the invention to eliminate the need for preliminary testing, for example of purity, of polypeptide factors necessary for the host cells in cell culture. Yet another object of this invention is to lower the risk of contamination of a cell culture by eliminating the need of adding exogenous factors. Another object is to produce a more robust host cell line by providing autocrine production of polypeptide factors necessary for the survival and growth of recombinant host cells in culture. A further object is to produce recombinant host cells that are less sensitive to medium conditions. Still another object is to provide a localized environment for cell growth or survival. Yet another object is to improve the efficiency of cell culture through autocrine production of necessary polypeptide factors. And yet another advantage is to the lower the cost of the defined medium.

SUMMARY OF THE INVENTION

The objects of this invention are accomplished by a novel method for culturing a recombinant host cell comprising: selecting a polypeptide-dependent host cell that requires a polypeptide factor for its survival or growth; transforming the host cell with a nucleic acid encoding the particular polypeptide factor; transforming a host cell with nucleic acid encoding a desired protein; and, culturing the transformed host cells in a medium lacking the particular polypeptide factor. The cells made in accord with this invention can survive or grow in a medium lacking the polypeptide factor. The recombinant host cell itself is satisfying its need for the polypeptide factor. It was not appreciated until the instant invention that a host cell could be made using recombinant means to supply the polypeptide factor(s) necessary for its own survival or growth in culture. Surprisingly, supply of the necessary polypeptide factor did not limit the host cell's capability to produce the desired protein in usable quantities. This invention provides significant economic savings in the culture of recombinant cells. This savings in the context of large scale production of a desired protein is on the order of tens of millions of dollars. Accordingly, in one aspect the invention is directed to a method for culturing a host cell in a medium lacking necessary polypeptide factor(s) for survival or growth. In another aspect the invention is directed to a host cell transformed to express a polypeptide factor necessary for its own growth or survival. Yet another aspect of the invention is the culture comprising polypeptide factor-transformed host cells in a medium lacking the polypeptide factor(s) necessary for the host cells' growth and maintenance.

(b) Growth of two insulin-independent cell lines and the control cell line in 1% charcoal/dextran extracted FBS (treated to remove insulin from the medium).

Figure 6A:
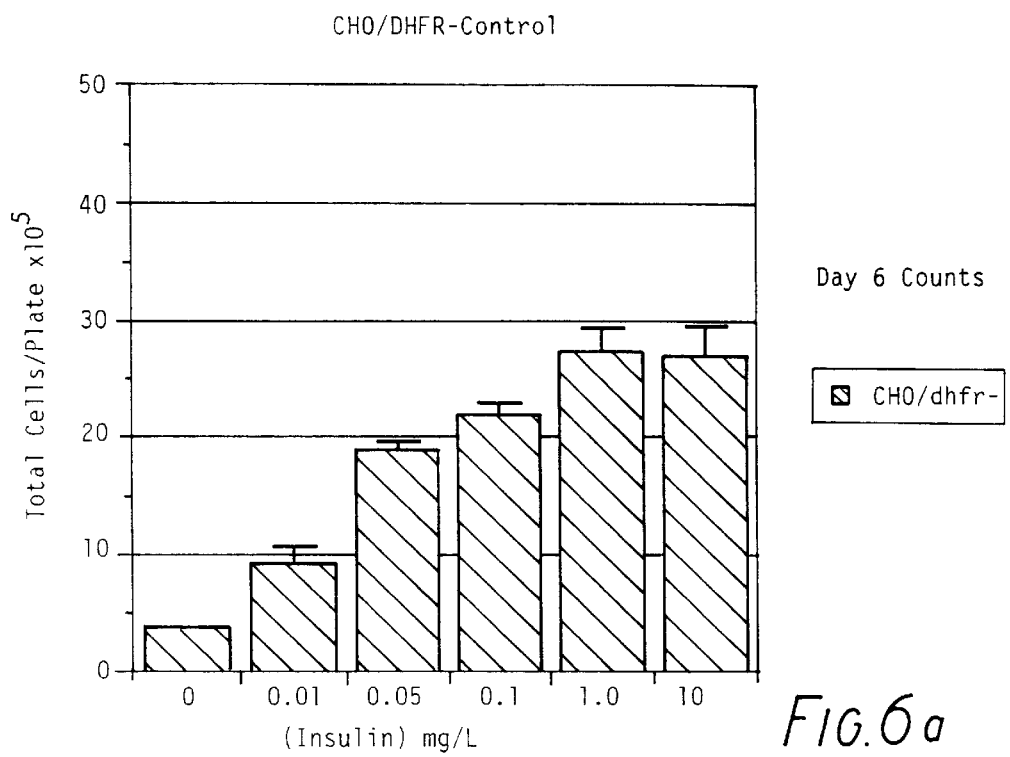
Figure 6B:
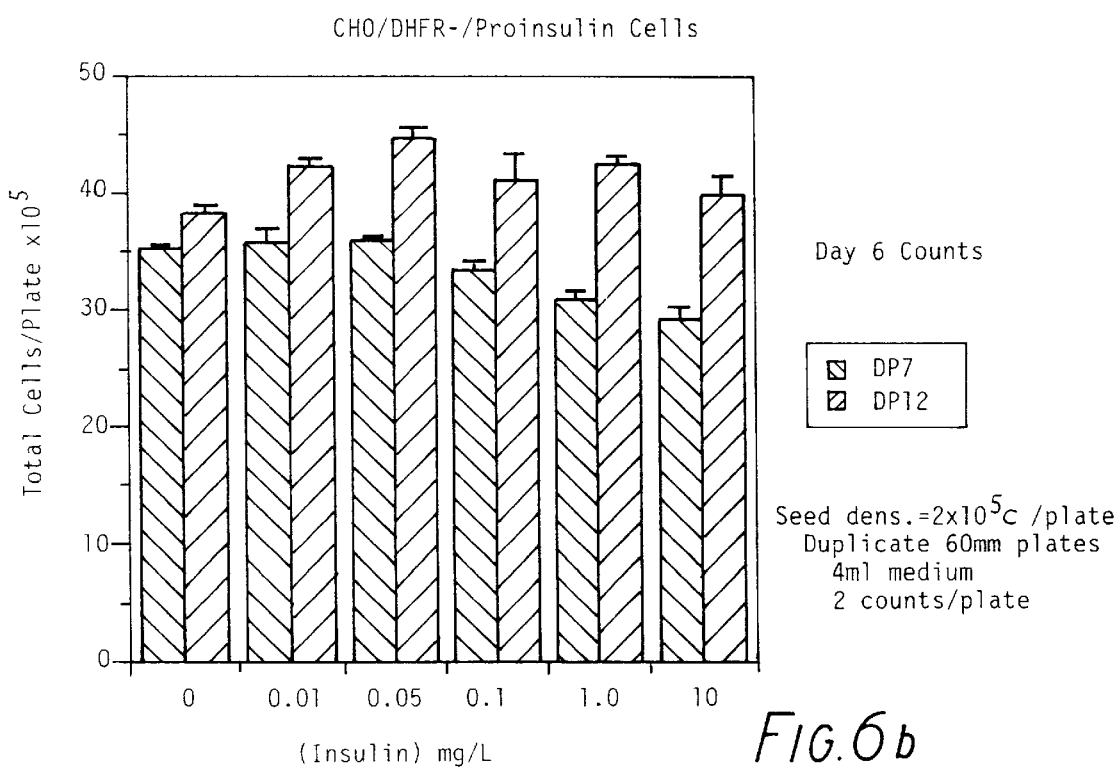

FIG. 6. (a) Growth of control cells (CHO/DHFR$^-$, no preproinsulin) in serum-free medium in the presence of 0 to 10 µg/ml exogenous insulin.

(b) Typical growth pattern of clones 7 and 12 subjected to varying insulin concentration under serum-free conditions.

Figure 7:
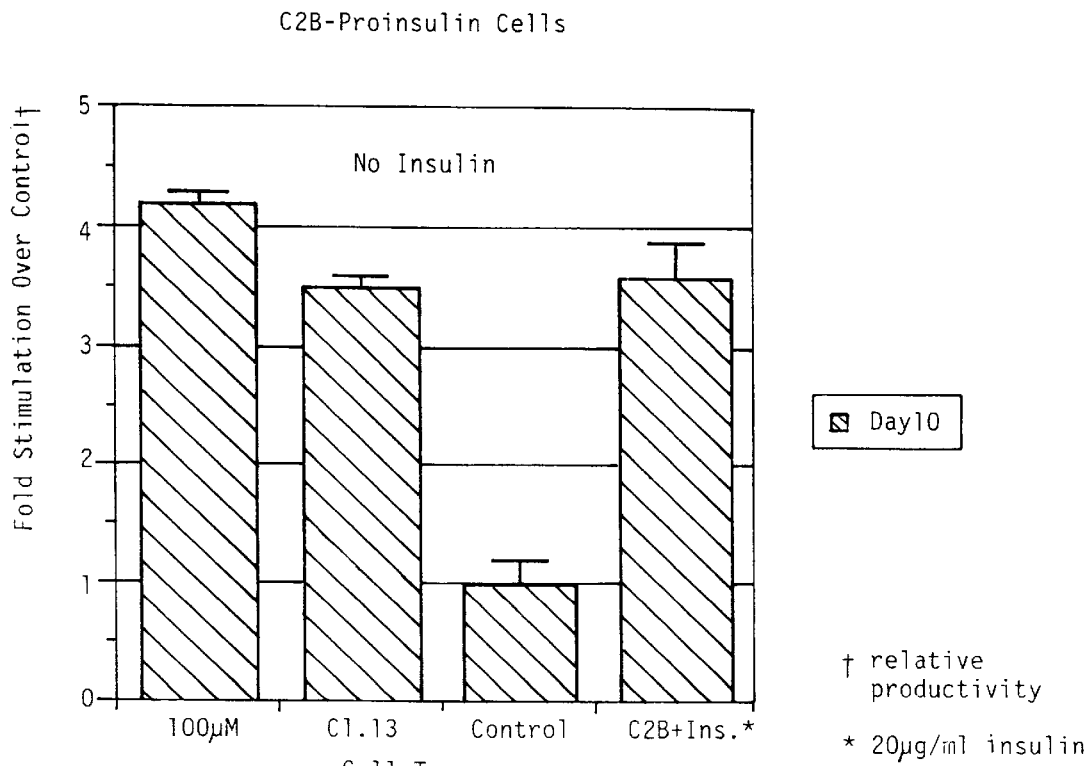

FIG. 7. In serum-free culture in the absence of insulin the DFMO pool (100 µM) and the unamplified clone 13 C2B-proinsulin line (Cl.13) which was selected for insulin independence demonstrated titers that were vastly elevated over C2B (control) under identical conditions. The C2B/clone 13 cell ultimately achieved tPA titers equivalent to the C2B control with 20 µg/ml insulin (C2B+insulin).

Figure 8:
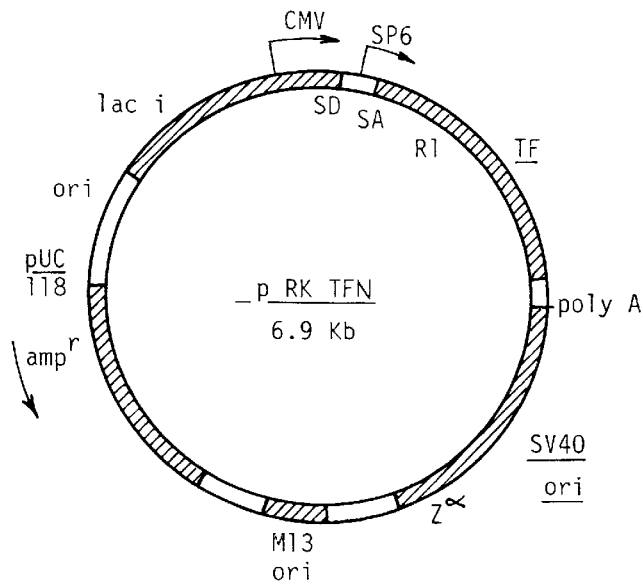

FIG. 8. Diagram of an expression vector, pRKTF, encoding transferrin.

Figure 9:
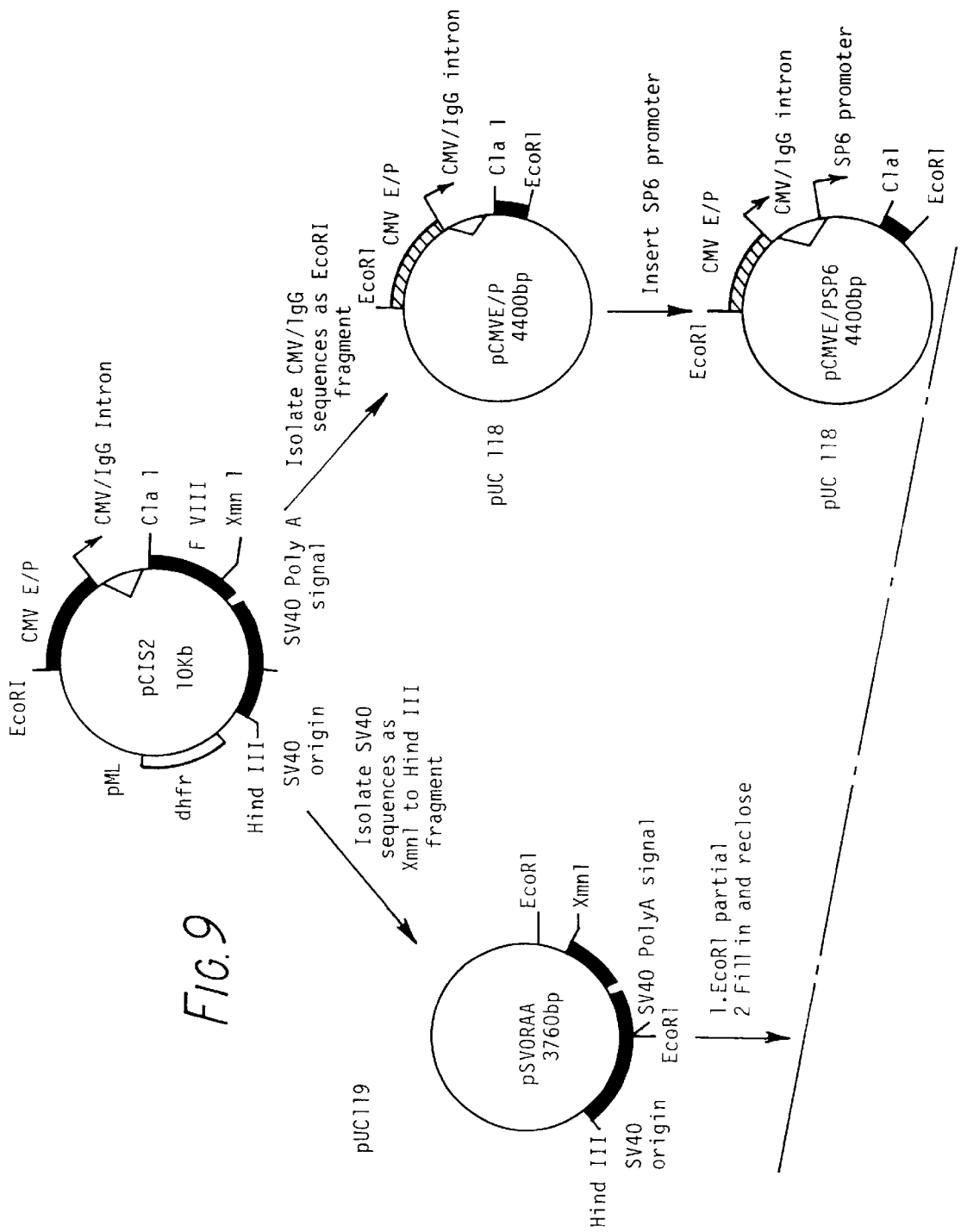
Figure 9:
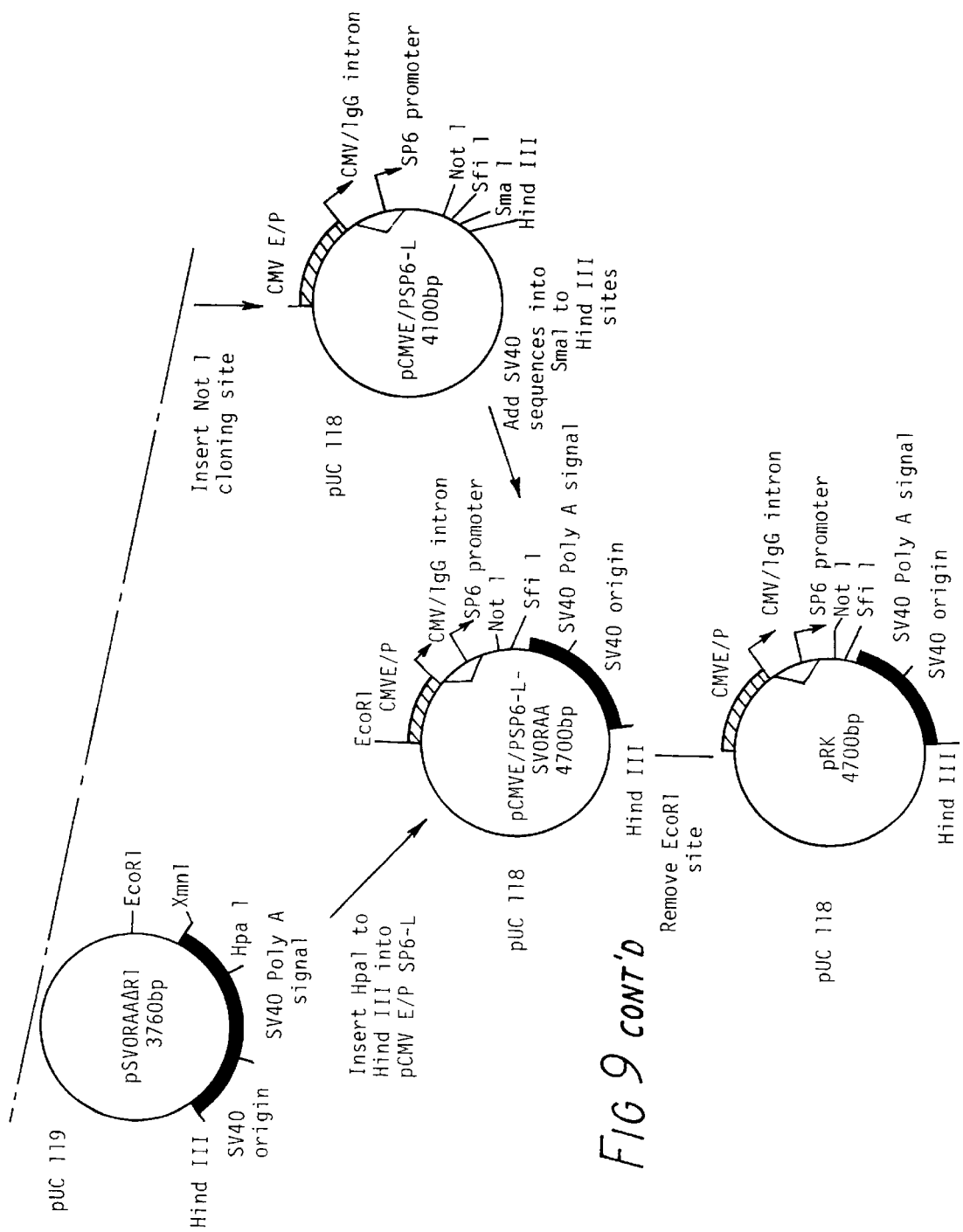

FIG. 9. Construction of the Expression vector pRK5 into which the cDNA encoding transferrin was inserted.

DETAILED DESCRIPTION

As used herein, "polypeptide factor," refers to any protein necessary for the survival or growth of a host cell in culture. The polypeptide factor may be a hormone, growth factor, peptide hormone, autocrine factor, transport protein, oncogene/proto-oncogene and the like. Examples of polypeptide factors that are hormones are, for example, insulin, proinsulin, follicle stimulating hormone (FSH), calcitonin, leutinizing hormone (LH), glucagon, parathyroid hormone (PTH), thyroid stimulating hormone (TSH), thyroid releasing hormone (TRH), growth hormone. Additional examples of polypeptide factors are the transport proteins, such as, transferrin, serum albumin, ceruloplasm, low density lipoprotein (LDL) and high density lipoprotein (HDL). Other examples of polypeptide factors, often described as autocrine because, in some instances, the cell they are secreted from can respond to the secreted factor, are interleukin-2, insulin, insulin-like growth factor I and II, transforming growth factor alpha (TGF-α), platelet-derived growth factor (PDGF), bombesin, erythropoietin, transforming growth factor-beta (TGF-β), sarcoma growth factor (SGF), epidermal growth factor (EGF), fibroblast growth factor (FGF), thrombin, nerve growth factor, hemopoietic growth factor and granulocyte-macrophage colony stimulating factor (GM-CSF). Yet other examples of polypeptide factors are peptides resulting from the expression of certain oncogenes/proto-oncogenes. The proteins encoded by these proto-oncogenes which come within the polypeptide factors of this invention are growth factors, transducing proteins and membrane receptors. Examples of a growth factor is PDGF (β subunit) encoded by the sis oncogene. Examples of peripheral membrane proteins are the truncated cell surface receptor for EGF encoded by erb-B, the cell surface receptor for M-CSF/CSF-1 encoded by fms and the receptors encoded by neu and ros. An example of a transducing protein is tyrosine kinase at the inner surface of the plasma-membrane encoded by abl. While these polypeptide factors encoded by oncogenes/proto-oncogenes are typically not added to a culture medium, they may be substituted for another polypeptide factor which is necessary. The growth factors of this invention are non-enzymatic and thus do not include such proteins as dihydrofolate reductase (DHFR), ornithine decarboxylase (ODC), thymidine kinase or phosphotransferase.

"Desired protein" refers to a protein which is desired to be expressed in a host cell, but which the host cell either normally does not produce itself or produces in small amounts, and which is not normally necessary for the cells' continued existence. The desired protein includes a protein having as few as about five amino acids to much larger proteins such as factor VIII. Such a protein includes any molecule having the pre- or prepro- amino acid sequence as well as amino acid or glycosylation variants (including natural alleles) capable of exhibiting a biological activity in common with the desired protein. Examples of such proteins are: growth hormone, insulin, factor VIII, tissue plasminogen activator, tumor necrosis factor alpha and beta, lymphotoxin, enkephalinase, human serum albumin, mullerian inhibiting substance, relaxin, tissue factor protein, inhibin, erythropoietin, interferon alpha, beta and gamma, superoxide dismutase, decay accelerating factor, viral antigen such as, for example, a portion of the AIDS envelope, and interleukin. The desired protein could also be a polypeptide factor.

The term "cell culture" or "culture" refers to populations of vertebrate cells grown from a single cell such that the population grows or survives for one or more generations. The growth or survival of vertebrate cells in culture, sometimes referred to as tissue culture, has become a routine procedure. See for example *Mammalian Cell Culture, The Use of Serum-Free Hormone-Supplemented Media*, Ed. Mather, J. P. (Plenum Press, N.Y., 1984).

The term "host cell" refers to those vertebrate cells capable of growth in culture and expressing a desired protein and a polypeptide factor(s). Suitable host cells include for example: monkey kidney CV1 line transformed by SV40 (COS-7, ATCC CRL 1651); human embryonic kidney line (293, Graham, F. L. et al., J. Gen Virol. 36: 59 [1977]); baby hamster kidney cells (BHK, ATCC CCL 10); chinese hamster ovary-cells-DHFR (CHO, Erlaub and Chasin, PNAS (USA) 77:4216 [1980]\0; mouse Sertoli cells (TM4, Mather, J. P., Biol. Reprod. 23:243–251 [1980]); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TR1 cells (Mather, J. P. et al., Annals N.Y. Acad. Sci. 383:44–68 [1982]). While the preferred host cells of this invention are vertebrate cells, other eukaryotic cells may be used, such as for example, insect cells.

The host cells may be transformed with nucleic acid encoding the polypeptide factor either before, after or simultaneously with nucleic acid encoding the desired protein. It is preferred to introduce the nucleic acid encoding the polypeptide factor before thus providing a "polypeptide factor-independent host cell" capable of being transformed with the nucleic acid encoding a desired protein.

"Polypeptide factor-dependent host cell" refers to a host cell requiring one or more polypeptide factors in the culture medium for growth or survival. The polypeptide factor(s) for a particular host cell is determined using general methods known to the ordinarily skilled artisan as described below. Elimination of the polypeptide factor from the medium may result in death of the cell or in inhibited growth. Which result depends upon the particular host cell, the polypeptide factor, culture conditions and other factors such as cell density.

The term "medium" refers to the aqueous environment in which the vertebrate cells are grown in culture. The medium comprises the physicochemical, nutritional, and hormonal environment. Traditionally the medium has been formulated by the addition of nutritional and growth factors necessary for growth or survival. "Serum-free medium" refers to a medium lacking serum. The hormones, growth factors, transport proteins, peptide hormones and the like typically found in serum which are necessary for the survival or growth of particular cells in culture are typically added as a supplement to serum-free medium. A "defined medium" refers to a medium comprising nutritional and hormonal requirements necessary for the survival and growth of the cells in culture such that the components of the medium are known. A defined medium provided by the method of the instant invention establishes a local environment for a particular host cell that may differ from the general environment of the medium.

Determining the particular polypeptide factor(s) and in turn providing a defined medium required by a recombinant host cell can be accomplished by the ordinarily skilled artisan in cell culture. Cell lines are routinely carried in a serum-supplemented medium. Most established cell lines have been grown in serum-supplemented medium for a period of years. It can be assumed that to a greater or lesser extent the serum-supplement is providing these cells with the hormones required for growth and survival in vivo and/or the cells have adapted to the absence of, or reduced levels of, some hormones required.

There are several approaches to defining the polypeptide factor requirements for a given cell line. The method of choice will depend on the cell line. Several possibilities are known to the ordinarily skilled artisan of which the following are exemplary. The initial step is to obtain conditions where the cells will survive and/or grow slowly for 3–6 days. In most cell types this is, in part, a function of inoculum density. For a cell which will attach and survive in serum-free media, it is only necessary to select the proper inoculum density and begin testing hormones for growth-promoting effects. Once the optimal hormone supplement is found, the inoculum density required for survival will decrease. In some cases the plating efficiency in hormones will be similar to that in serum, although this is not true for all cell types. This may be due to added requirements for attachment factors or growth factors needed only initially or at higher concentrations than those needed when cells are plated at high densities. Many cells, both transformed and normal, are capable of producing substances which are required for their attachment or growth.

However, some cell lines will not survive even 24 hours or will not attach to the dish in serum-free medium. For these cells several initial approaches are possible: pre-coat the dish with serum; plate cells in serum-containing medium for 12–24 hours and then change to serum-free; reduce serum concentrations to the point where the cells will survive but not grow; and use various attachment factors.

The various polypeptide factors can then be tested under these minimal conditions. When optimal conditions for growth are found, the serum (or pre-incubation step) can then be omitted and/or replaced with purified attachment and/or polypeptide factors.

Cells in serum-free medium generally require insulin and transferrin in a serum-free medium for for optimal growth. These two factors should be tested first. Most cell lines require one or more of the growth factors. These include epidermal growth factor (EGF), fibroblast growth factor (FGF), insulin like growth factors I and II (IGFI, IGFII), nerve growth factor (NGF), etc. Other classes of factors which may be necessary include: prostaglandins; steroids; transport and binding proteins (e.g., ceruloplasmin, high and low density lipoprotein [HDL, LDL], albumin); hormones; and fatty acids.

Polypeptide factor testing is best done in a stepwise fashion testing new polypeptide factors in the presence of those found to be growth stimulatory. This is essential in some cases as polypeptide factor effects are seldom simply additive. Alternatively, some polypeptide factors can stimulate growth singly but their effects when added together cancel or are inhibitory.

A complete replacement of serum by polypeptide factor would ideally allow for a doubling time and plating efficiency equal to (or in some cases greater than) that seen for that cell type in serum and the ability to carry the cell line through successive subcultures in the polypeptide factor-supplemented serum-free medium. It would be expected that the dose of each polypeptide factor added should fall within the physiologic range for that factor. It should be noted, however, that this is not always the case. In some cases a higher level is required (e.g., insulin at 5–10 μg/ml) and in others, a lower range (e.g., TF 0.50–50 μg/ml). Finally, a more highly purified preparation of added polypeptide factors may elicit a different response than a less pure form. Additionally, the optimal amount of a given polypeptide factor added to the media may vary in different media, for cells grown on different substrates, or in the presence of other polypeptide factors.

For undefined media it is sufficient to grow cells in conditions in which the polypeptide factor is known to be absent or inactive (e.g., depleted serum) (Nishikawa et al. Proc. Natl. Acad. Sci. USA 72:483–487 [1975]; Kato et al. Exptl. Cell Res. 130:73–81 [1980]; McAuslan et al. Exptl. Cell Res. 128:95–101 [1980]; and Ross et al. Cell 14:203–210 [1978]) The growth of cells in the presence or absence of the polypeptide factor can then be measured to determine whether the factor is required for growth stimulation or survival. The polypeptide factor tested should be of sufficient purity to be able to conclude with reasonable certainty that it is, in fact, the known peptide which is responsible for the growth stimulation.

"Control region" refers to specific sequences at the 5' and 3' ends of eukaryotic genes which may be involved in the control of either transcription or translation. Virtually all eukaryotic genes have an AT-rich region located approximately 25 to 30 bases upstream from the promoter, the site where transcription is initiated. Another sequence found 70 to 80 bases upstream from the start of transcription of many genes is a CXCAAT region where X may be any nucleotide. At the 3' end of most eukaryotic genes is an AATAAA sequence which may be the signal for addition of the poly A tail to the 3' end of the transcribed mRNA.

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication. Fiers et al., Nature, 273: 113 (1978). The immediate early promoter of the human cytomegalovirus is conveniently obtained as a HindIII E restriction fragment. Greenaway, P. J. et al., Gene 18: 355–360 (1982). Of course, promoters from the host cell or related species also are useful herein.

Transcription of a DNA encoding a polypeptide factor or desired protein by higher eukaryotes is increased by inserting an enhancer sequence into the vector. Enhancers are cis-acting elements of DNA, usually about from 10–300 bp, that act on a promoter to increase its transcription. Enhancers are relatively orientation and position-independent having been found 5' (Laimins, L. et al., PNAS 78: 993 [1981]) and 3' (Lusky, M. L., et al., Mol. Cell Bio. 3: 1108 [1983]) to the transcription unit, within an intron (Banerji, J. L. et al., Cell 33: 729 [1983]) as well as within the coding sequence itself (Osborne, T. F., et al., Mol. Cell Bio. 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells, including vertebrate host cells, will also contain sequences necessary for the termination of transcription which may affect mRNA expression. These regions are transcribed as polyadenylated segments in the untranslated portion of the mRNA encoding the polypeptide factor or the desired protein. The 3' untranslated regions also include transcription termination sites.

Expression vectors for expression of the desired protein or the polypeptide factor may contain a selection gene, also termed a selectable marker. Examples of suitable selectable markers for mammalian cells are dihydrofolate reductase (DHFR), thymidine kinase or phosphotransferase. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR⁻ cells and mouse LTK⁻ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., J. Molec. Appl. Genet. 1: 327 (1982), mycophenolic acid, Mulligan, R. C. and Berg, P. Science 209: 1422 (1980) or hygromycin, Sugden, B. et al., Mol.

Cell. Biol. 5: 410–413 (1985). The three examples given above employ bacterial genes under eukaryotic control to convey resistance to the appropriate drug G418 or neomycin (geneticin), xgpt (mycophenolic acid) or hygromycin, respectively.

"Amplification" refers to the increase or replication of an isolated region within a cell's chromosomal DNA. Amplification is achieved using a selection agent e.g. methotrexate (MTX) which inactivates DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and the DHFR or amplification gene permitting cointegration. One ensures that the cell requires more DHFR, which requirement is met by replication of the selection gene, by selecting only for cells that can grow in the presence of ever-greater MTX concentration. So long as the gene encoding a desired heterologous protein has cointegrated with the selection gene replication of this gene gives rise to replication of the gene encoding the desired protein. The result is that increased copies of the gene, i.e. an amplified gene, encoding the desired heterologous protein express more of the desired heterologous protein.

"Transformation" means introducing DNA into an organism so that the DNA is replicable, either as an extrachromosomal element or by chromosomal integration. Unless indicated otherwise, the method used herein for transformation of the host cells is the method of Graham, F. and van der Eb, A., Virology 52: 456–457 (1973). However, other methods for introducing DNA into cells such as by nuclear injection, protoplast fusion, electroporation or liposomes may also be used. If prokaryotic cells or cells which contain substantial cell wall constructions are used, the preferred method of transfection is calcium treatment using calcium chloride as described by Cohen, F. N. et al., Proc. Natl. Acad. Sci. (USA), 69: 2110 (1972).

Construction of suitable vectors containing the desired coding and control sequences employ standard recombinant DNA techniques. Isolated plasmids or DNA fragments are cleaved, tailored, and religated in the form desired to form the plasmids required.

For analysis to confirm correct sequences in plasmids constructed, the ligation mixtures are used to transform *E. coli* K12 strain 294 (ATCC 31446) and successful transformants selected by ampicillin or tetracycline resistance where appropriate. Plasmids from the transformants are prepared, analyzed by restriction and/or sequenced by the method of Messing et al., Nucleic Acids Res. 9: 309 (1981) or by the method of Maxam et al., Methods in Enzymology 65: 499 (1980).

"Transfection" refers to the taking up of an expression vector by a host cell whether or not any coding sequences are in fact expressed. Numerous methods of transfection are known to the ordinarily skilled artisan, for example, CaPO$_4$ and electroporation. Successful transfection is generally recognized when any indication of the operation of this vector occurs within the host cell.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 5 to 8 percent polyacrylamide gel described by Goeddel, D. et al., Nucleic Acids Res., 8: 4057 (1980).

"Dephosphorylation" refers to the removal of the terminal 5' phosphates by treatment with bacterial alkaline phosphatase (BAP). Alternatively, calf alkaline phosphatase in BRL cove restriction buffer could be used. This procedure prevents the two restriction cleaved ends of a DNA fragment from "circularizing" or forming a closed loop that would impede insertion of another DNA fragment at the restriction site. Procedures and reagents for dephosphorylation are conventional. Maniatis, T. et al., *Molecular Cloning* pp. 133–134 (1982). Reactions using BAP are carried out in 50 mM Tris at 68° C. to suppress the activity of any exonucleases which may be present in the enzyme preparations. Reactions were run for 1 hour. Following the reaction the DNA fragment is gel purified.

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with ATP in the presence of a nucleotide kinase. A synthetic oligonucleotide will ligate to a fragment that has not been dephosphorylated.

"Ligation" refers to the process of forming phosphodiester bonds between two double stranded nucleic acid fragments (Maniatis, T. et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

"Filling" or "blunting" refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2–15 µg of the target DNA in 10 mM MgCl$_2$, 1 mM dithiothreitol, 50 mM NaCl, 10 mM Tris (pH 7.5) buffer at about 37° C. in the presence of 8 units of the Klenow fragment of DNA polymerase I and 250 µM of each of the four deoxynucleoside triphosphates. The incubation generally is terminated after 30 min. phenol and chloroform extraction and ethanol precipitation.

Host cells are transformed with vector(s) expressing the polypeptide factor and the desired protein and cultured in a conventional manner. Various cell culture systems are known to the ordinarily skilled artisan. For example, plate systems grow cells attached to a surface. Solid support matrices, such as steel, glass, organic polymer or ceramic material, contained in a culture chamber may be used. Another system consisting of a suspension of microcarrier beads with attached anchorage-dependent cells, or of cells grown within or trapped in suspended bead matrices may also be used. Yet another system is suspension culture which provides ease of monitoring conditions and scale-up potential. The choice of culture system would be made by one of ordinary skill after considering several variables, such as: the particular host cell and whether that cell is anchorage-dependent; manipulations to be performed, various cell properties such as, for example, lactic acid production; whether secretion is density-dependent; the desired protein to be produced by the host cell; and, the volume in which the culture is to be maintained.

The following examples merely illustrate the best mode now known for practicing the invention, but should not be construed to limit the invention. All literature citations herein are expressly incorporated by reference.

Example 1

Construction of Human Proinsulin Expression Vector

The cDNA clone of the insulin gene, pHI3, provided the coding sequence of the human preproinsulin gene for construction of plasmids to direct the expression of preproinsulin in transfected mammalian cells. The vector pSVE-HIGDHFR containing the SV40 promoter, the cDNA encoding human preproinsulin, the hepatitis B virus surface antigen polyadenylation site and the cDNA encoding mouse dihydrofolate reductase was constructed.

Figure 1:
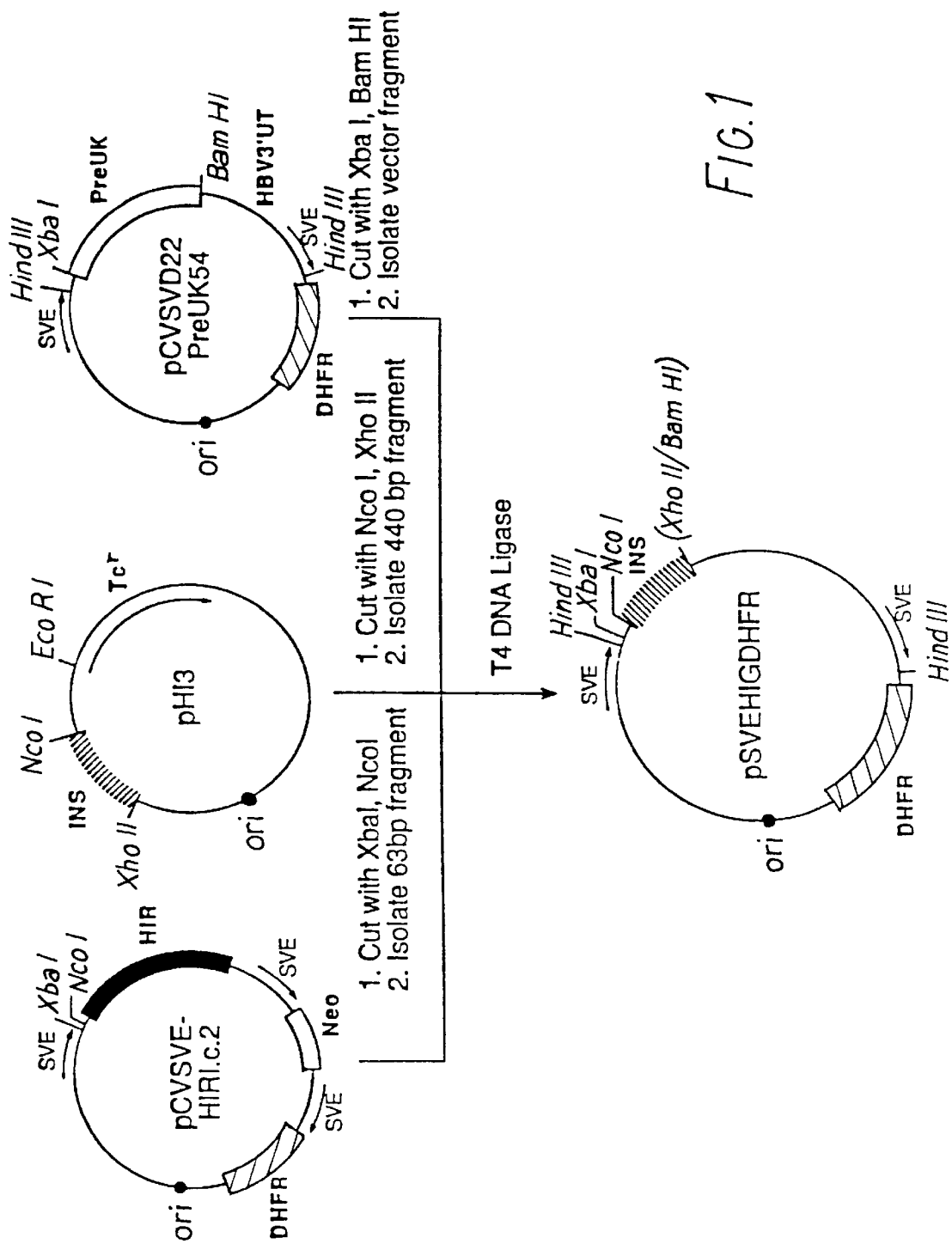
FIG. 1. Construction of a human preproinsulin expression vector, pSVEHIGDHFR, used to establish an insulin-independent cell line for production of a desired protein.

FIG. 1 shows the steps for construction of the preproinsulin expression vector used to establish an insulin-independent host cell line. The three parts of the construction of pSVEHIGDHFR are detailed below:

a) pSVEHIGDHFR

1) The cDNA encoding human preproinsulin was obtained in a 440 bp fragment from pHI3 by a (NcoI-XhoII) digest. pHI3 is described in Sures, I. et al., Science 208:57 (1980). The 440 bp fragment containing the cDNA encoding preproinsulin was isolated.

2) A 63 bp XbaI-NcoI fragment was isolated from the 5' end of the insulin receptor plasmid (pCVSVE-HIRc-2, European Publication No. 0192392, published Aug. 27, 1986). This fragment functioned as a linker-adapter to fuse the 5' end of the cDNA encoding preproinsulin to the SV40 early promoter.

Figure 2:
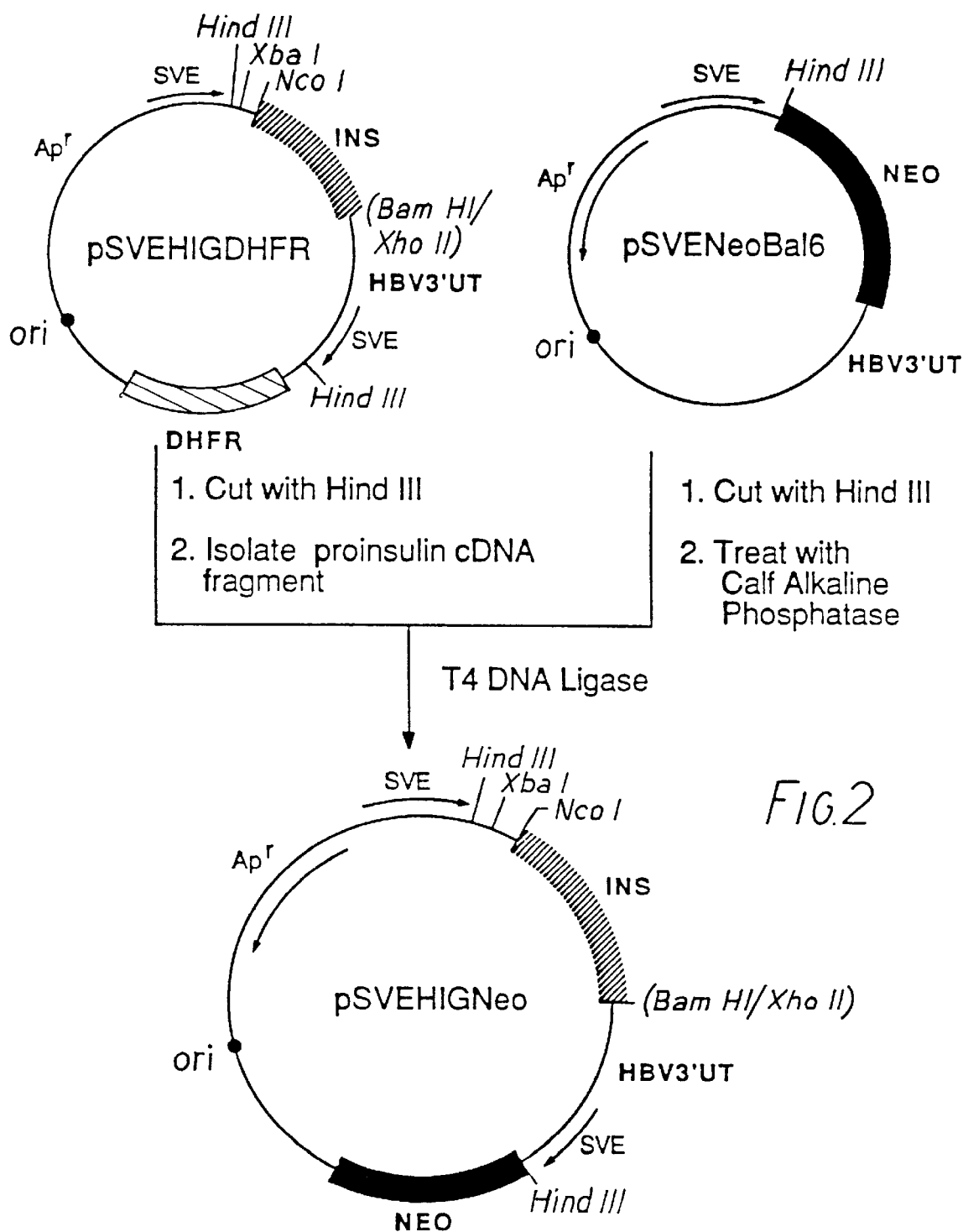
FIG. 2. Construction of a human preproinsulin expression vector, pSVEHIGNeo, used to establish an insulin-independent cell line for production of a desired protein.

3) The vector, pCVSVD22/preUK54, providing the plasmid backbone which is ligated to the 63 bp linker and preproinsulin gene coding sequences was prepared as described below. pCVSVD22/preUK54, the plasmid backbone, is the product of a three fragment ligation as diagramed in FIG. 2.

i) The SV40 early promoter is obtained by digesting plasmid pCVSVE-HBV (European Patent Application Publication No. 0117060, published Aug. 29, 1984) with PvuI and XbaI.

ii) The fragment containing the preurokinase cDNA was obtained from plasmid p preUK54 trp207-I (European Patent Application Publication No. 0092182, published Oct. 26, 1983). The plasmid was digested with ClaI. The ClaI ends are made blunt by a filling reaction. The Klenow fragment of DNA polymerase I plus all 4 deoxyribonucleotide triphosphates are added to fill in the ClaI protruding single stranded ends. After the fill-in, plasmid DNA is digested with the second enzyme, XbaI. The XbaI-ClaI (filled) preUK54 cDNA fragment was then isolated.

iii) The vector fragment containing the bacterial origin of replication, the DHFR cDNA, eukaryotic expression unit, and the 3' untranslated region of hepatitis virus surface antigen was derived from pEHED22 (U.S. Pat. No. 4,624,918, issued Nov. 25, 1986). The plasmid was first cut with BamHI. The protruding BamHI ends were then blunted by a filling reaction with Klenow DNA polymerase I as in the procedure detailed for ClaI blunting described above. Following the BamHI digestion and fill-in, the DNA was cut with XbaI and the large 4.3 Kb fragment isolated.

These three fragments were mixed together and ligated in a three fragment, concerted ligation. The recombinant pCVSVD22/preUK54 was recovered. Ligation of a filled ClaI site to a filled BamHI site results in an intact BamHI site at this junction.

To construct pSVEHIGDHFR, pDVSVD22/preUK54 was digested with XbaI and BamHI and the vector fragment isolated.

The final three part ligation to yield pSVEHIGDHFR used: a) the 440 bp NcoI-XhoII fragment containing the cDNA for preproinsulin; b) a 63 bp XbaI-NcoI fragment from pCVSVE-HIRc-2 to link the cDNA to the SV40 early promoter; and, c) the XbaI-BamHI vector fragment from pCVSVD22/preUK54 containing the SV40-DHFR transcription unit, the ampicillin resistance marker origin of replication in *E. coli*, the hepatitis surface antigen 3' end with the polyadenylation and transcription termination site. The three fragments were ligated together in a concerted three-way ligation and transformed into *E. coli*. Transformants were analyzed and the desired recombinant identified.

b) pSVEHIGNeo

Figure 3:
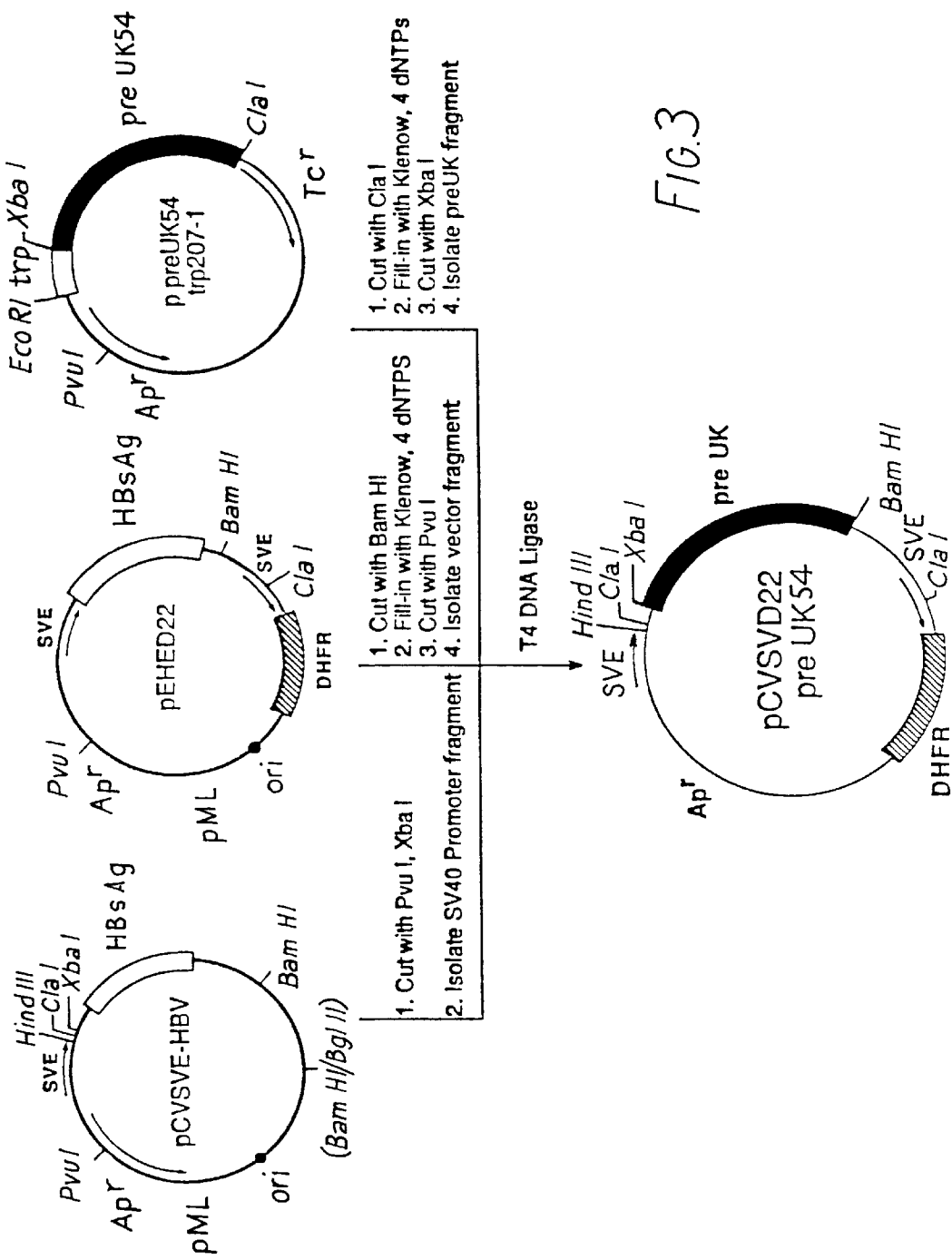
FIG. 3. Construction of pSVEHI6Neo for expression of proinsulin.

FIG. 3 shows the steps for construction of the preproinsulin expression vector pSVEHIGNeo.

This vector was constructed via a two fragment construction. The first fragment was a HindIII fragment from pSVE-HIGDHFR described above. Included in the fragment was the cDNA encoding preproinsulin and the SV40 early promoter that initiates transcription of the DNA encoding DHFR. The plasmid backbone comprising the second fragment was obtained by digestion at the unique HindIII site just downstream of the SV40 promoter of pSVENEOBal6 (European Publication No.0160457, published Nov. 6, 1985). The linearized plasmid was then treated with calf alkaline phosphatase to prevent recircularization. The HindIII fragment from pSVEHIGDHFR was inserted at the unique HindIII site of pSVENeoBal6 such that the SV40 promoter originally transcribing the mouse SV40-DHFR transcription unit is upstream of the preproinsulin gene. After ligation the plasmid is transformed into *E. coli* 294 cells.

Recombinant cells are identified by restriction analysis to insure proper orientation of the fragment containing the preproinsulin cDNA. In the proper orientation the SV40 promoter which originally transcribed the bacterial Neo gene is now upstream and initiates transcription of the preproinsulin cDNA.

c) pEO

A vector containing the ornithine decarboxylase (ODC) cDNA under control of the SV40 promoter, having a hepatitis B polyadenylation sequence and an ampicillin gene for selection in E. coli, was constructed. The endogenous ODC gene can be amplified in mammalian cells by selection with the ODC inhibitor, alpha difluoromethylornithine (DFMO). (McConlogue, L. & Coffino, P., J. Biol. Chem. 258, 8384–8388 [1983]; McConlogue, L. & Coffino, P., J. Biol. Chem. 258:12083–12086 [1983]).

Figure 4:
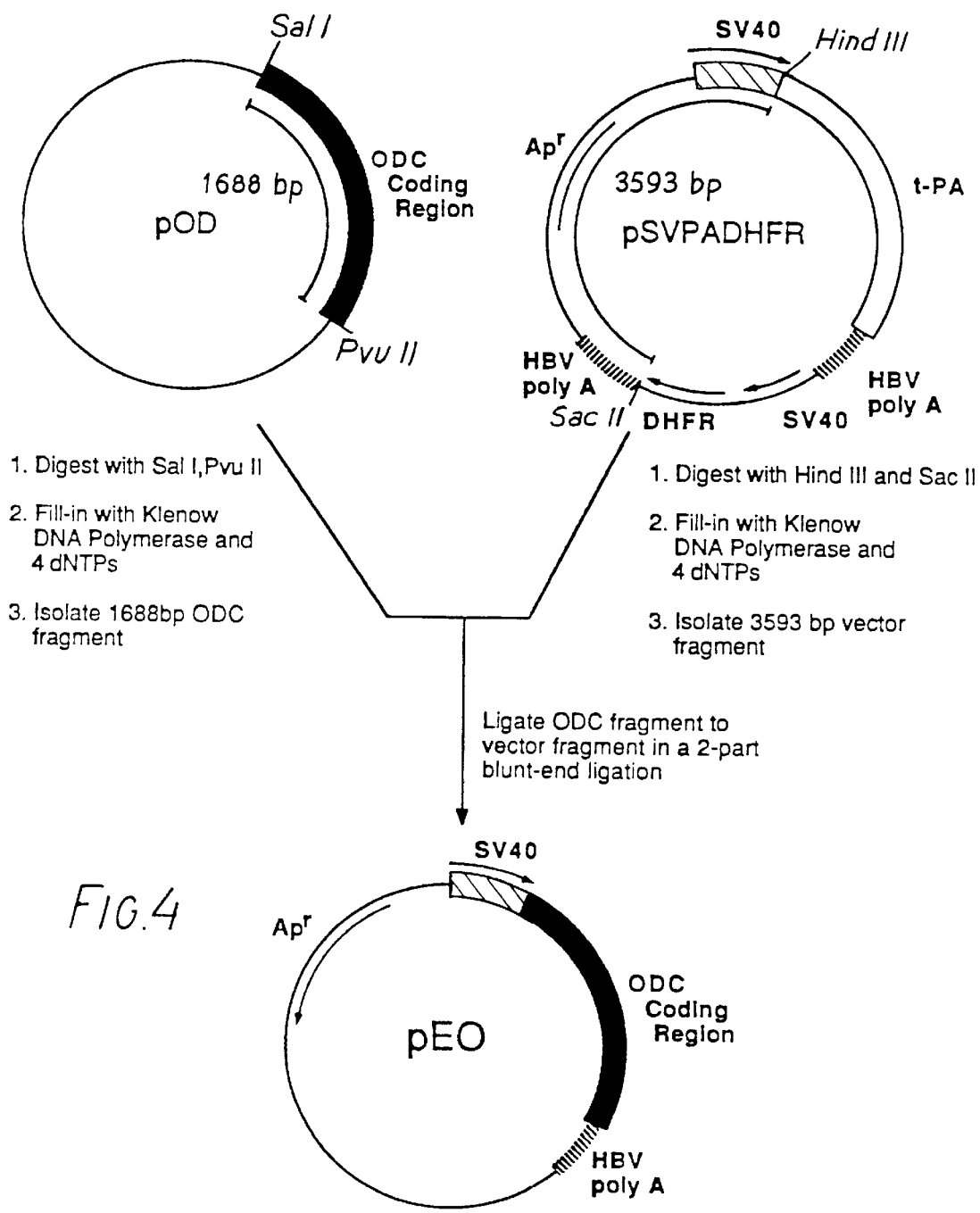
FIG. 4. Construction of an ornithine decarboxylase (ODC) expression vector used for amplification of the ODC gene and the cotransfected preproinsulin gene.

FIG. 4 shows the steps for construction of pEO via a two fragment ligation.

1. A 1688 bp ODC fragment containing the entire coding region of ODC was obtained from a plasmid containing ODC cDNA cloned into pBR322 (McConlogue, L. et al. Proc. Natl. Acad. Sci. USA 81:540–544 [1984]; Gupta, M & Coffino, P. J. Biol. Chem. 260:2941–2944 [1985]). The plasmid was cut with SalI and PvuII. The ends were blunted by filling in with Klenow, and the 1688 pair ODC fragment was isolated on a gel.

2. A 3593 bp fragment containing the SV40 early promoter, the hepatitis polyadenylation sequence, and the AMP gene for selection in E. coli was isolated from plasmid pSVPADHFR. (European Patent Application Publication No. 0,093,619, referred to therein as pETPFR which was modified by the addition of 192 bp fragment at the SV40 promoter 5' to the DNA encoding tPA. The additional 192 bp fragment included an extra HindIII site.) The plasmid was cut with HindIII and SacII and the ends were filled in with Klenow DNA polymerase and the 3593 fragment was isolated on a gel.

These two fragments were then ligated together in a two-part ligation to form pEO. (See FIG. 4). The orientation and configuration of the fragments in the final plasmid was checked by restriction analysis.

Example 2

Selection of Insulin-Independent Cells

Determination of the requirement for particular polypeptide factor, in this case proinsulin, for a polypeptide factor-dependent host cell, in this case CHO cells, was done by supplementing insulin-free medium with proinsulin. It was known that most cells require insulin to survive in serum-free media. (Sato, G. H. et al., supra). Surprisingly, proinsulin was shown to be a replacement for insulin in the case of the CHO host cell in culture. Thus CHO/DHFR$^-$ cells were transfected with the preproinsulin vector to provide proinsulin in an autocrine fashion.

CHO/DHFR$^-$ cells were transformed with the pSVEHI6Neo plasmid by calcium phosphate precipitation (Simonsen, C. C. & Levinson, A. D., PNAS 80:2495–2499 [1983]) and were selected for insulin-independent growth by passaging the cells at low density into serum-free (350m Osm), insulin-free F-12/DME (Gibco) medium (SFIF). F-12/DME comprises: high glucose; 1× GHT (0.01 g/1-glycine, 0.015 g/1-hypoxanthine, and 0.005 g/l thymidine); 10 mNM HEPES; 1.0 mg/L transferrin; trace elements (McKeehan, W. L. et al. PNAS 72:2023 [1976]; Johnson Mathew Chemicals); 1 uM linoleic acid; 1×10$^{-10}$ M T3 and 1×10$^{-8}$M hydrocortisone, estradiol and progesterone. After two weeks in this medium, surviving cells were rescued with medium containing 5% dialyzed, charcoal-dextran DEAE extracted, heat-treated FBS (ChX-FBS). The CHO DHFR$^-$ cells will grow in whole serum but not ChX-FBS unless supplemented with insulin. The ChX-FBS is, however, capable of providing other necessary factors as can be seen by comparing the growth rate in the presence of ChX-FBS+ insulin compared to insulin alone. Thus, the addition of ChX-FBS alone would lead to an increased replication rate ("rescue") of those cells which were providing their own proinsulin. Processing of the serum using charcoal extraction was necessary to remove active insulin. Thus, the sole source of insulin was the transformed host cell. Insulin-independent cells were cloned on the basis of colony morphology and size. Clones were subsequently screened for insulin-independent growth in 1% ChX-FBS. Under insulin-free conditions the parent line is severely limited in its ability to replicate (1–2 divisions/week) while the transformed clones exhibited a 30–40 fold increase in cell number in the same time period.

Two clones which demonstrated the capacity to survive and grow when carried under insulin-free conditions over extended periods of time were labelled DP 7 and DP 12, respectively. These insulin-independent cells were further selected in SFIF in spinners and on plates. Those cells placed in spinners (500 ml) were inoculated at 1×10$^5$ cells/ml in SFIF. Plated cells (100 mm plates) were at a seeding density of 2×10$^5$ cells/60 mm plate. After nearly two weeks of selection for insulin-independence, surviving cells were rescued from both the plates and the spinners, with medium containing 5% dialyzed, extracted FBS. Cells from the spinner cultures were removed at that time to plates. Cells were cloned by limiting dilution using serial dilutions. The cells from these colonies were then serially diluted to 1 cell/well. All cloning was done in the presence of F-12/DME, high glucose, 5% charcoal extracted FBS medium. Approximately one month later, cells which grew out of the initial cloning were again serially diluted to one cell/well. The clones which survived and grew were then taken to 100 mm plates. These cells were carried in SFIF plus 500 nM methotrexate and subcultured weekly.

Figure 5A:
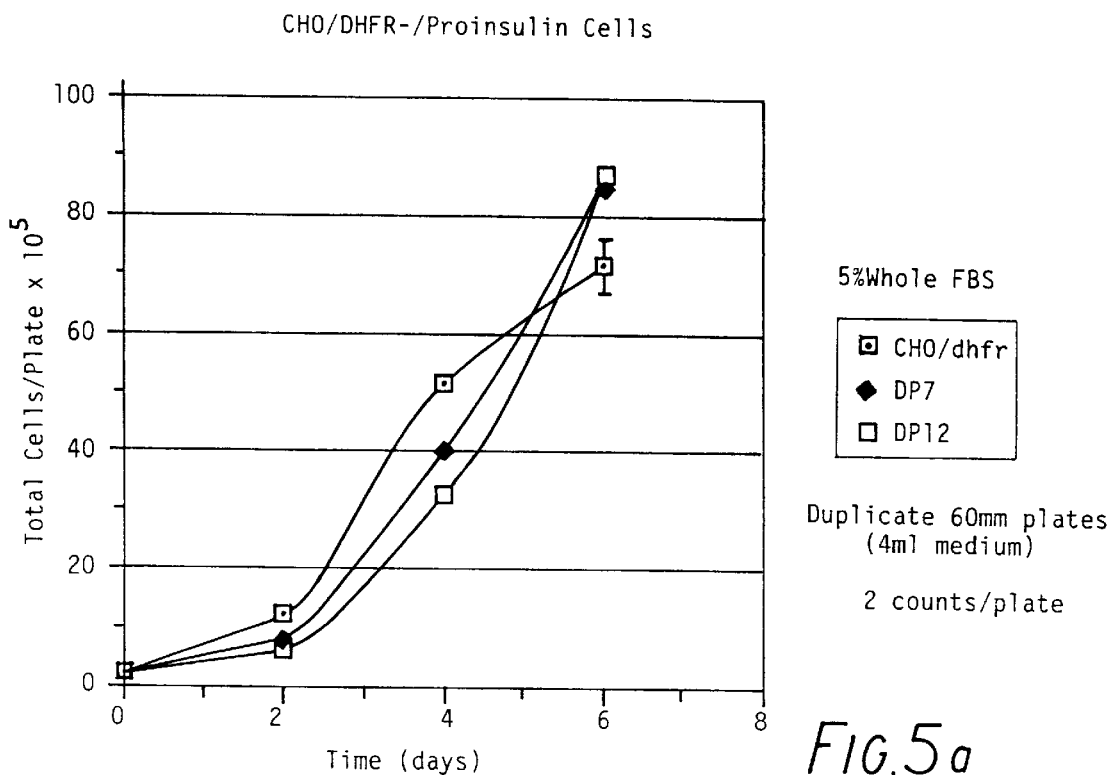
FIG. 5. (a) Growth of two insulin-independent cell lines and control cell line in presence of 5% whole FBS.
Figure 5B:
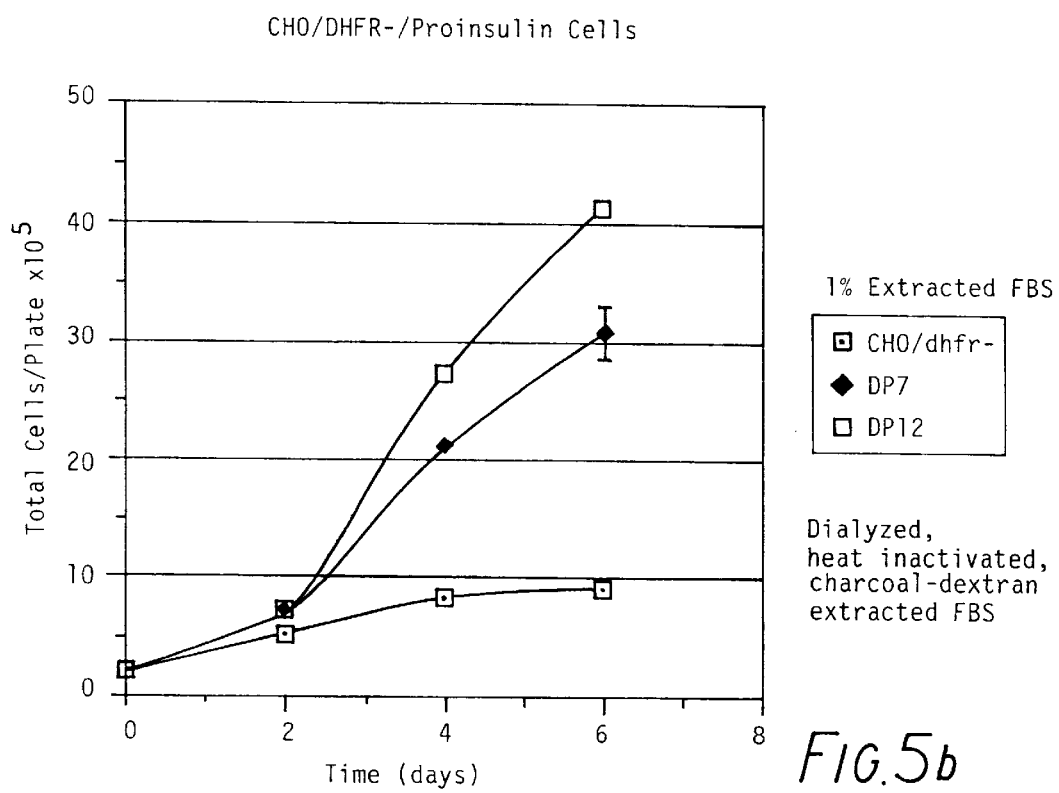

Clones DP 7 and 12 demonstrated the capacity to survive and grow. As shown in FIG. 5 the insulin-independent cells were able to survive and grow in an insulin-free milieu while the control cells were not. The insulin-independence of the cells of this invention is shown in FIG. 6. As the concentration of insulin in the medium is reduced growth of the insulin-independent cell line is maintained while the number of cells/plate for the control cells declined with decreasing concentration of insulin in the medium.

Example 3 tPA Production by an Insulin-Independent Cell Line

Expression of t-PA in the culture medium was assayed quantitatively in a radioimmunoassay. Purified tPA and purified iodinated tracer tPA were diluted serially to include concentration of 12.5 to 400 ng/ml in phosphate buffered saline, pH 7.3, 0.5 percent bovine serum albumin, 0.01 percent Tween 80, and 0.02 percent sodium azide. Appropriate dilutions of medium samples to be assayed were added to the radioactively labelled tracer proteins. The antigens were allowed to incubate overnight at room temperature in the presence of a 1:10,000 dilution of the IgG fraction of a rabbit anti-tPA antiserum. Antibody-antigen complex was precipitated by absorption to goat anti-rabbit IgG Immunobeads (Biorad) for two hours at room temperature. The beads were cleared by the addition of saline diluent followed by centrifugation for ten minutes at 2000×g at 4° C. Supernatants were discarded and the radioactivity in the precipitates was monitored. Concentrations were assigned by comparison with the reference standard. It has been shown that various polypeptide factors affect protein secretion as well as affecting survival or growth of the host cell. Polypeptide factors such as follicle stimulating hormone (FSH), epidermal growth factor (EGF), insulin and transferrin have been shown to effect protein secretion from cultured cells. (Rich, K. A. et al. Endocrinology 113(6):2284 [1983]). Thus, a transformed host cell (C2B) producing a desired protein, tissue plasminogen activator, was made insulin-independent to assess production/secretion of the desired protein.

In order to determine whether endogenously produced proinsulin would be sufficient to support the secretion of a desired protein (e.g. tPA) in an insulin-independent fashion, a transfection was performed in a manner similar to that described in example 2, but using a host cell previously transformed to express a desired protein, in this case tPA. The vector, pSVEHIGNeo, described in example 1 was transfected into the CHO cell line containing amplified tPA and DHFR (referred to as C2B) (European Publication No. 0093619). Transfection was by the calcium-phosphate coprecipitation method. (Simonsen, C. C. & Levinson, A. D., PNAS 80:2495–2499 [1983]; Wigler, M. et al., PNAS [USA] 76:1242–1255 [1979]). Transfected cells expressing the Neo gene were selected by growth in medium containing G418.

The C2B preproinsulin transfected cells were selected for insulin independence in serum-free, insulin-free (SFIF) spinners and plates. The serum-free medium was standard 350mOsm insulin-free F-12/DME medium described above: glucose; 2×GHT; 10 mM Hepes; 1.0 Mg/L transferrin; 1× trace elements; 1 µM linoleic; 1×10$^{-10}$M T$_3$ and 1×10$^{-8}$M hydrocortisone, estradiol and progesterone.

After nearly two weeks of selection for insulin-independence, surviving cells were rescued from both the plates and the spinners with medium containing 5% dialyzed, extracted FBS, and 23 clones were derived by limiting dilution. These clones were screened for tPA production under serum-free conditions in the absence of insulin and in the presence of varying insulin concentrations (including the optimal concentration of 20 µg/ml insulin). Clone 13 was picked as the most promising for further work.

An alternative method for the creation of an insulin-independent cell to the transfection/selection described in Example 2 and immediately above is by amplification and in turn increased expression of proinsulin. Thus, C2B cells producing tPA were cotransfected with the pSVEHIGNeo vector described in Example 1(b) and the pEO vector of example 1(c). This would permit amplification using DFMO after selection. A similar cotransfection-coamplification methodology is described by Simonsen, C. C. and Levinson, A. D., supra.

The C2B cells cotransfected with the preproinsulin-Neo vector and the ODC vector, pEO, were first selected in medium containing G418. G418 resistant cells were then grown in increasing concentrations, 25, 100, 300 and 500 µM DFMO to amplify the transfected ODC gene and coamplify the preproinsulin gene. After this amplification procedure methotrexate was added to the medium with DFMO to maintain selective pressure on the amplified tPA, the desired protein. The C2B preproinsulin transfected cells were tested for insulin-independence in serum-free, insulin-free (SFIF) spinners and plates. The serum-free medium was standard 350mOsm insulin-free F-12/DME medium described above: glucose; 2×GHT; 10 mM Hepes; 1.0 Mg/L transferrin; 1× trace elements; 1 µM linoleic; 1×10$^{-10}$M T$_3$ and 1×10$^{-8}$M hydrocortisone, estradiol and progesterone.

FIG. 5 shows the production of r-tPA by the CHO insulin-independent cells transfected with the preproinsulin gene and selected and the alternative method comprising transfection with pSVEHIGNeo and amplification. C2B (control) cells, C2B/clone 13 insulin-independent cells and the 100 µM DFMO amplified pool were rinsed three times in SFIF medium and resuspended in SFIF medium. Clone 13 and the 100 µM DFMO insulin-independent cell lines produced tPA in the absence of insulin at titers equivalent to those achieved by the C2B control cell line in the presence of optimal concentrations of insulin.

Example 4

Construction of Transferrin Expression Vector a) Isolation of Human Transferrin cDNA Messenger RNA (mRNA) was prepared from the liver of an adult male accident victim by guanidine thiocyanate homogenization/lithium chloride precipitation (Cathala, G. et al. DNA 2:329 [1983]).

Double-stranded complementary DNA (ds-cDNA) was synthesized using the above mRNA as a template and employing a commercially available kit utilizing oligo(dT)-priming (Amersham Corporation) according to the manufacturer's instructions (which are based on Okayama, H., and Berg, P., Mol. Cell. Biol. 2:161 [1982] and Gubler, U. and Hoffman, B. J., Gene 25:263 [1983]).

DNA oligonucleotide linkers were ligated to both ends of the blunt-ended ds-cDNA as shown:

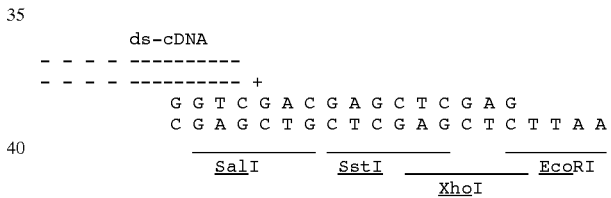

yielding ds-cDNA terminating in EcoRI restriction sites.

The ds-cDNA was fractionated by polyacrylamide gel electrophoresis and the ds-cDNA migrating above 2000 base pairs was recovered from the gel by electroelution. The size-fractionated ds-cDNA was ligated into the bacteriophage lambda vector gt10 (Hyunh, T. V. et al. in *DNA Cloning Techniques, A Practical Approach,* D. Glover (ed.) [IRL Press, Oxford, 1985]) that had been cut with EcoRI and packaged using a commercial bacteriophage lambda packaging extract (Stratagene).

The packaged bacteriophage were plated on *E. coli* strain C600 hfl$^-$ (Hyunh, T. V. et al. Construction and Screening cDNA Libraries in λ gt10 and λ gt11 in DNA Cloning ed. Glover, D. M., [IRL Press Oxford, Washington, D.C.], [1985])., and bacteriophage DNA was transferred to replicate nitrocellulose filters (Maniatis, T. et al. *Molecular Cloning: A Laboratory Manual,* [Cold Spring Harbour Laboratory, 1982]).

b) Identification of Recombinant Clones Containing the Transferrin cDNA

Six of the nitrocellulose filters were probed with the synthetic oligonucleotide shown below. Its sequence was designed to hybridize to the sequence of the human trans ferrin cDNA from nucleotide #110 to #175 as reported by Yang et al. Proc. Natl. Acad. Sci. [USA] 81:2752–2756 (1984).

5' GTG TGC AGT GTC GGA GCA TGA GGC CAC TAA GTG
CCA-GAG TTT CCC CGA CCA TAT GAA AAG CGT CA 3'

The oligonucleotide was radiolabelled by the addition of a radioactive phosphate group to the 5' end of the oligonucleotide in a standard kinase reaction (Maniatis, T. et al., supra at 125). The hybridization was carried out as described by Maniatis, (Ibid pg. 326) using 30% formamide in the hybridization buffer. Positively hybridizing plaques were identified using autoradiography (Maniatis, Ibid pg. 326) and six individual phage plugs were picked for purification (Maniatis, Ibid pg 64).

The phage from each plug were replated at low density and after a 16 hour growth phase bacteriophage DNA was again transferred to nitrocellulose filters. These filters were screened as described above using the same oligonucleotide probe. A single isolated plaque was picked from each of the six plates. These phage were used to infect a culture of a susceptible strain of *E. coli*, c600 hFI⁻ (Hyunh, T. V. et al., supra).

Phage DNA was prepared from each of the six clones using a standard small scale phage preparation (Maniatis, Ibid pg. 373).

40 μg of DNA from each clone was digested with the restriction enzyme, SstI (Goff, S. P. and Rambach, A., Gene 3:347 [1978]). These digests were run out on 1% low melting point agarose gels (Struhl, K., Biotechniques 3:452 [1985]). Three of the clones showed inserts of approximately the correct size of 2.3 Kb (Yang et al., supra). The insert bands were cut out of the gels and subcloned (Struhl, supra) into the M13 based vector mp19 (Yanish-Perron et al., Gene 33:103–119 [1985] and Norrander, J. et al., Gene 26:101 [1983]). Recombinant phage clones (white plaques) were picked and the ends sequenced.

One of the clones showed perfect coding region identity to the published transferrin sequence (Yang et al., supra). The insert from this clone was subcloned (Struhl, supra) into pUC19 (Yanish-Perron, supra) in the SstI site. Recombinant clones were identified as white colonies on plates containing transferrin-gal (Yanish-Perron, supra). Plasmid DNA was purified from a single clone in which the transferrin coding region was oriented in the direction opposite the lacZ promoter region.

The transferrin coding region was excised from the pUC vector as a 2.3 Kb EcoRI-XbaI fragment from an XbaI-EcoRI partial digest. This unique fragment was purified from a 1% low melting point gel and subcloned (Struhl, supra) into an EcoRI-XbaI digested pRK5 vector. Construction of this vector is described below and in FIG. 9. This created pRKTFN.

c) Construction of pRK5

The starting plasmid was pCIS2.8c28D (described in copending U.S. patent applications Ser. No. 07/071,674 and 06/907,297). The base numbers in paragraphs 1 through 6 refer to pCIS2.8c28D with base one of the first T of the EcoRI site preceding the CMV promoter. The cytomegalovirus early promoter and intron and the SV40 origin and polyA signal were placed on separate plasmids.

1. The cytomegalovirus early promoter was cloned as an EcoRI fragment from pCIS2.8c28D (9999-1201) into the EcoRI site of pUC118 (Yanish-Perron et al. Gene 33:103 [1985]). Twelve colonies were picked and screened for the orientation in which single stranded DNA made from pUC118 would allow for sequencing from the EcoRI site at 1201 to the EcoRI site at 9999. This clone was named pCMVE/P.

2. Single stranded DNA was made from pCMVE/P in order to insert an SP6 (Green, M. R. et al., Cell 32:681–694 [1983]) promoter by site-directed mutagenesis. A synthetic 110 mer which contained the SP6 promoter (See Nucleic Acids Res. 12:7041 [1984] FIG. 1; sequences from −69 to +5 of SP6 promoter were used along with 18 bp fragments on either end of the oligomer corresponding to the CMVE/P sequences. Mutagenesis was done by standard techniques and screened using a labeled 110 mer at high and low stringency. Six potential clones were picked and sequenced. A positive was identified and labelled pCMVE/PSP6.

3. The SP6 promoter was checked and shown to be active, for example, by adding SP6 RNA polymerase and checking for RNA of the appropriate size.

4. A Cla-NotI-Sma adapter was made to be inserted from the ClaI site (912) to the SmaI site of pUC118 in pCMVE/P (step 1) and pCMVE/PSP6 (step 2). This adapter was ligated into the ClaI-SmaI site of pUC118 and screened for the correct clones. The linker was sequenced in both and clones were labelled pCMVE/PSP6-L and pCMVE/P-L.

5. pCMVE/PSP6-L was cut with SmaI (at linker/pUC118 junction) and HindIII (in pUC118). A HpaI (5573) to HindIII (6136) fragment from pSVORAAΔRI 11, described below, was inserted into SmaI-HindIII of pCMVE/PSP6-L. This ligation was screened and a clone was isolated and named pCMVE/PSP6-L-SVORAAΔRI.

a) The SV40 origin and polyA signal was isolated as XmnI (5475)-HindIII (6136) fragment from pCIS2.8c28D and cloned into the HindIII to SmaI sites of pUC119. This was named pSVORAA.

b) The EcoRI site at 5716 was removed by partial digest with EcoRI and filling in with Klenow. The colonies obtained from self-ligation after fill-in were screened and the correct clone was isolated and named pSVORAAΔRI 11. The deleted EcoRI site was checked by sequencing and shown to be correct.

c) The HpaI (5573) to HindIII (6136) fragment of pSVORAAΔRI 11 was isolated and inserted into pCMVE/PSP6-L (see 4 above).

6. pCMVE/PSP6-L-SVOrAAΔRI (step 5) was cut with EcoRI at 9999, blunted and self-ligated. A clone without an EcoRI site was identified and named pRK.

7. pRK was cut with SmaI and BamHI. This was filled in with Klenow and religated. The colonies were screened. A positive was identified and named pRKΔBam/Sma 3.

8. The HindIII site was converted to a HpaI site using a converter. (A converter is a piece of DNA used to change one restriction site to another. In this case one end would be complimentary to a HindIII sticky end and at the other end have a recognition site for HpaI.) A positive was identified and named pRKΔBam/Sma, HIII-HpaI 1.

9. pRKΔBam/Sma, HIII-HpaI 1 was cut with PstI and NotI and a RI-HIII linker and HIII-RI linker were ligated in. Clones for each linker were found. However, it was also determined that too many of the HpaI converters had gone in (two or more converters generate a PvuII site). Therefore, these clones had to be cut with HpaI and self-ligated.

10. RI-HIII clone 3 and HIII-RI clone 5 were cut with HpaI, diluted, and self-ligated. Positives were identified. The RI-HIII clone was named pRK5.

Example 5

Selection of Transferrin-Independent Cells

DP7 insulin-independent cells were transfected with pRKTFN described in example 4 above. Transfection was by the calcium phosphate coprecipitation method of Simonsen and Levinson, supra. Transfected cells are selected for hygromycin-resistance. The hygromycin-resistant cell pool is cloned and several colonies are picked. Cloning decreases the possibility of cross-feeding non-producer cells in the subsequent selection step. Cell lines making transferrin are selected by growing the above clones in a serum-free (350m Osm) transferrin-free F-12/DME medium. F-12/DME is as described above, except that no iron is added. However, under these conditions iron is introduced as a contaminant of other medium components (e.g. water, NaCl, etc.). This small amount of iron is insufficient to support optimal cell growth in the absence of transferrin, but can support cell growth in the presence of transferrin (Mather, J. P. and Sato, G. H., Exptl. Cell Res. 120:191–200 [1979]; Perez-Infante, U. and Mather, J. P., Exptl. Cell Res. 142:325–332 [1982]) presumably due to increased efficiency of iron-uptake via the transferrin-receptor system. Cells which survive for 1–2 weeks in this serum-free/transferrin-iron-free medium are then rescued with F-12/DME medium containing 5% extracted FBS. Clones are subsequently tested for transferrin independence by comparing the growth of the clones and the untransfected parent line in the low-iron medium with and without added human transferrin. Clones with the capacity to survive and grow when carried under transferrin-iron-free conditions are selected further in spinners and plates.

The selected transferrin-independent clones are subsequently tested for insulin-independence by comparing the growth of those clones and the untransfected lines in serum-free, insulin-free, transferrin-free and low iron medium with and without insulin and transferrin.

What is claimed is:

1. A method for culturing a mammalian host cell comprising:

a) transforming the host cell with a first nucleic acid sequence encoding and capable of expressing a polypeptide comprising insulin.

b) transforming the host cell with a second nucleic acid sequence encoding and capable of expressing a desired protein not required for growth or survival of the host cell; and c) culturing the doubly transformed host cell in a medium lacking sufficient exogenous insulin for survival or growth of the step b) transformed host cell.

2. The method of claim 1 which additionally comprises the step of recovering the desired protein from the host cell culture.

3. The method of claim 1 wherein the medium is serum-free medium.

4. The method of claim 1 wherein the desired protein is selected from the following: growth hormone, insulin, factor VIII, tissue plasminogen activator, tumor necrosis factor alpha, tumor necrosis factor beta, lymphotoxin, enkephalinase, human serum albumin, mullerian inhibiting substance, relaxin, tissue factor protein, inhibin, erythropoietin, interferon alpha, interferon beta, interferon gamma, superoxide dismutase, decay accelerating factor, viral antigen, AIDS viral envelope protein, or interleukin.

5. The method of claim 1 wherein the host cell is further transformed with a selection gene.

6. The method of claim 5 wherein the selection gene encodes dihydrofolate reductase, thymidine kinase, or phosphotransferase.

7. The method of claim 5 wherein the selection gene encodes a polypeptide that confers host cell resistance to neomycin, mycophenolic acid, or hygromycin.

* * * * *